US009970046B2

(12) United States Patent
Ieko et al.

(10) Patent No.: US 9,970,046 B2
(45) Date of Patent: *May 15, 2018

(54) METHOD OF MEASURING BLOOD COAGULATION TIME TO DETECT LUPUS ANTICOAGULANTS

(75) Inventors: Masahiro Ieko, Sapporo (JP); Chizuru Morikawa, Tokyo (JP); Keiko Hattori, Ibaraki (JP)

(73) Assignees: SCHOOL JURIDICAL PERSON HIGASHI-NIPPON-GAKUEN, Ishikari-gun (JP); SEKISUI MEDICAL CO., LTD., Tokyo (JP)

( * ) Notice: Subject to any disclaimer, the term of this patent is extended or adjusted under 35 U.S.C. 154(b) by 239 days.

This patent is subject to a terminal disclaimer.

(21) Appl. No.: 14/127,041

(22) PCT Filed: Jun. 15, 2012

(86) PCT No.: PCT/JP2012/065434
§ 371 (c)(1),
(2), (4) Date: Jan. 10, 2014

(87) PCT Pub. No.: WO2012/173260
PCT Pub. Date: Dec. 20, 2012

(65) Prior Publication Data
US 2014/0127726 A1 May 8, 2014

(30) Foreign Application Priority Data
Jun. 17, 2011 (JP) ................................. 2011-135174

(51) Int. Cl.
G01N 33/86 (2006.01)
C12Q 1/56 (2006.01)
G01N 33/564 (2006.01)

(52) U.S. Cl.
CPC ............. C12Q 1/56 (2013.01); G01N 33/564 (2013.01); G01N 33/86 (2013.01); G01N 2800/104 (2013.01); G01N 2800/24 (2013.01)

(58) Field of Classification Search
CPC ................ G01N 33/86; G01N 33/564; G01N 2800/104; G01N 2800/224; G01N 2800/24; G01N 33/20; G01N 33/4905; G01N 33/6854; G01N 33/92; G01N 35/025; C12Q 1/56
See application file for complete search history.

(56) References Cited

U.S. PATENT DOCUMENTS

| 4,056,484 | A | 11/1977 | Heimburger et al. |
| 4,877,741 | A | 10/1989 | Babcock et al. |
| 2002/0019021 | A1* | 2/2002 | Kraus .................. C12Q 1/56 435/13 |
| 2003/0044872 | A1* | 3/2003 | Okuda .................. G01N 33/52 435/13 |

FOREIGN PATENT DOCUMENTS

| CN | 1336178 A | 2/2002 |
| CN | 1780637 A | 5/2006 |
| CN | 101221189 A | 7/2008 |
| CN | 101675991 A | 3/2010 |
| CN | 101861142 A | 10/2010 |
| CN | 101903030 A | 12/2010 |
| CN | 102066417 A | 5/2011 |
| CN | 102066947 A | 5/2011 |
| EP | 0 482 088 B1 | 3/1999 |
| EP | 1 243 928 A1 | 9/2002 |
| EP | 1 707 634 A1 | 10/2006 |
| JP | 6 324048 | 11/1994 |
| WO | 01 48486 | 7/2001 |
| WO | 2007/018511 | 2/2007 |

OTHER PUBLICATIONS

Kagawa, K. (2006) Blood Coagulation Correction Test. Examination and Technology 34(8): 735-742.*
Tripodi et al. ((2007) Laboratory Testing for Lupus Anticoagulants: A Review of Issues Affecting Results. Clinical Chemistry 53(9): 1629-35.*
Teruya et al. ((2007) Lupus anticoagulant assays: questions answered and to be answered. Arch. Pathol. Lab. Med 131: 885-9.*
Extended European Search Report dated Jan. 23, 2015 in Patent Application No. 12801236.6.
Armando Tripodi "Laboratory Testing for Lupus Anticoagulants: A Review of Issues Affecting Results" Clinical Chemistry, vol. 53, No. 9, XP055161670, Sep. 2007, pp. 1629-1635.
Jun Teruya, et al., "Lupus Anticoagulant Assays: Questions Answered and to Be Answered" Archives of Pathology & Laboratory Medicine, vol. 131, XP055161669, Jun. 2007, pp. 885-889.
Toru Yoshimura, et al., "Stability of Pro-Gastrin-Releasing Peptide in Serum versus Plasma" Tumor Biology, vol. 29, No. 4, XP009131799, Sep. 2008, pp. 224-230.
U.S. Appl. No. 14/127,026, filed Jan. 10, 2014, Ieko, et al.
Combined Chinese Office Action and Search Report dated Jun. 12, 2015 in Patent Application No. 201280029832.5 (with English translation of categories of cited documents).
Combined Chinese Office Action and Search Report dated Nov. 15, 2014 in Patent Application No. 201280029832.5 (with English Translation of Category of Cited Documents).
Combined Office Action and Search Report dated Dec. 11, 2015 in Chinese Patent Application No. 201280029832.5 (with English translation of categories of cited documents).

(Continued)

Primary Examiner — Lisa J Hobbs
(74) Attorney, Agent, or Firm — Oblon, McClelland, Maier & Neustadt, L.L.P.

(57) ABSTRACT

Provided is a method of measuring blood coagulation time, the method being capable of LA detection easily and with high sensitivity as compared with the method recommended by the ISTH, without being affected by deficiency of blood coagulation factors even in a blood sample of a warfarin taker, a person who suffers from vitamin K deficiency, or a hepatic failure patient. Disclosed is a method of measuring the blood coagulation time to detect lupus anticoagulant, the method including adding a buffer solution composition containing blood coagulation factors to a blood sample before measurement or at the time of measurement of the blood coagulation time, and measuring the blood coagulation time.

18 Claims, 5 Drawing Sheets

(56) References Cited

OTHER PUBLICATIONS

Kagawa, K., "Blood Coagulation Correction Test", Examination and Techonology, vol. 34, No. 8, pp. 735-742, and 806, (Aug. 2006) (with English translation).

Ieko, M., et al, "Cross-Mixing Test to Detect Lupus Anticoagulant for Diagnosis of Antiphospholipid Syndrome" The Japanese Journal of Clinical Pathology, vol. 57, No. 10, pp. 990-998, (2009) (with partial English translation).

Kanno, N., et al., "Lupus Anticoagulant Sokutei no Tameno Kessho Kentai Sakusei to Kensa no Genjo", Modern Medical Laboratory, vol. 37, No. 13, pp. 1484-1490, (Dec. 2009).

Pengo, V., et al., "Update of the guidelines for lupus anticoagulant detection", Journal of Thrombosis and Haemostasis, vol. 7, pp. 1737-1740, (2009).

Written Opinion of the International Searching Authority dated Sep. 25, 2012 in PCT/JP12/65434 Filed Jun. 15, 2012.

International Search Report dated Sep. 25, 2012 in PCT/JP12/65434 Filed Jun. 15, 2012.

Combined Chinese Office Action and Search Report dated May 9, 2016 in Patent Application No. 201280029832.5 (with English language translation of categories of cited documents).

Subramanian Yegneswaran, et al., "Prothrombin amino terminal region helps protect coagulation factor Va from proteolytic inactivation by activated protein C", *Thromb Haemost.* Author manuscript, vol. 101, No. 1, 2009, pp. 1-16.

Office Action as received in the corresponding Indian Patent Application No. 10544/DELNP/2013 dated Jan. 23, 2018, 6 pages.

Perumal Thiagarajan, et al., "The Use of the Dilute Russell Viper Venom Time for the Diagnosis of Lupus Anticoagulants"; Blood, vol. 68, No. 4, 1986, pp. 869-874.

\* cited by examiner

METHOD OF MEASURING BLOOD COAGULATION TIME TO DETECT LUPUS ANTICOAGULANTS

CROSS REFERENCE TO RELATED APPLICATIONS

The present application is a 35 U.S.C. § 371 national stage patent application of International patent application PCT/JP2012/065434, filed on Jun. 15, 2012, published as WO/2012/173260 on Dec. 20, 2012, the text of which is incorporated by reference, and claims the benefit of the filing date of Japanese application no. 2011-135174, filed on Jun. 20, 2011, the text of which is also incorporated by reference.

TECHNICAL FIELD

The present invention relates to a method of measuring the blood coagulation time of a blood sample to be tested for the purpose of detecting lupus anticoagulant.

BACKGROUND ART

Measurement of the blood coagulation time is carried out for the screening of the presence or absence of any abnormality in the blood coagulation system, or for the measurement of the activity of individual blood coagulation factors, by measuring the time period starting from the time point at which a reagent for blood coagulation time measurement including an activating agent for blood coagulation factors (hereinafter, may be simply referred to as activating agent) and/or $Ca^{2+}$ and the like is added to a specimen blood or a specimen blood mixture, to the time point at which detectable fibrin clots are formed (blood coagulation time; hereinafter, may also be simply referred to as coagulation time. Also, formation of fibrin clots may also be simply referred to as coagulation). Typical examples of blood coagulation tests include prothrombin time (PT), activated partial thromboplastin time (APTT), and thrombin time. Hereinafter, in the present specification, blood coagulation factors may be simply referred to as coagulation factors.

PT is the time taken from the addition of a mixed liquid of tissue thromboplastin and $Ca^{2+}$ to a test plasma, to the occurrence of coagulation, and this is intended to comprehensively examine the coagulation activities of factor VII, factor X, factor V, prothrombin, fibrinogen, and the like that are associated with the extrinsic pathway of coagulation. Furthermore, APTT is the time taken from the addition of a sufficient amount of phospholipids and an activating agent (kaolin, anhydrous silicic acid, ellagic acid, or the like) and an appropriate amount of $Ca^{2+}$ to a test plasma, to the occurrence of coagulation, and this is intended to comprehensively examine the coagulation activity of factor XII, factor XI, prekallikrein, high molecular weight kininogen, factor IX, factor VIII, factor X, factor V, prothrombin, fibrinogen and the like, which are associated with the intrinsic pathway of coagulation. In general, what is referred to as abnormality in these blood coagulation tests refers to the prolongation of the coagulation time. Abnormality in the blood coagulation system reflects the signs or results of the tendency to hemorrhage or the tendency to thrombosis (tendency to blood coagulation) in the body.

Regarding the causes for the prolongation of the coagulation time, the following can be considered: 1) deficiency or a decrease in blood coagulation factors, 2) the presence of an antibody to a blood component that constitutes the blood coagulation system, 3) the presence of an antibody to a component in the reagent for blood coagulation time measurement, 4) the presence of an antibody to a complex of a blood component that constitutes the blood coagulation system and a component in the reagent for blood coagulation time measurement, and 5) administration of a drug that inhibits the blood coagulation reaction.

However, simply performing the measurement of the blood coagulation time does not enable discriminating whether the cause of the prolongation of the coagulation time is, for example, a decrease in the blood coagulation activity due to simple deficiency of coagulation factors, or a decrease in the blood coagulation activity due to inhibition of the coagulation reaction by an antibody (inhibitor) to a component that constitutes the blood coagulation system or a component in the reagent for blood coagulation time measurement. On the other hand, since the therapeutic policy varies with the difference in the relevant cause of prolongation, discrimination of the cause of prolongation is important. Thus, there has been a blood coagulation correction test (hereinafter, also may be referred to as "blending test" or "mixing test") in which for the purpose of determination of the cause of prolongation, normal plasma is added to a test plasma, and the extent to which the blood coagulation time of the test plasma is corrected (normalized) is plotted into a graph to determine the cause (Non-Patent Document 1).

Conventionally, the mixing test has been carried out, for example, in the manner described below.

Samples are prepared by adding and mixing normal plasma to a test plasma such that the mixing proportions of the normal plasma are 0%, 20%, 50%, 80% and 100%, and the APTT is measured. The results are plotted into a graph (horizontal axis: proportion of normal plasma incorporated or the proportion (%) of the test plasma, vertical axis: coagulation time (seconds)), and the cause of prolongation of the coagulation time is visually discriminated and determined from the shape of the graph. For example, when the test plasma is coagulation factor-deficient, the addition of a small amount of normal plasma (20% in FIG. 1(A)) significantly shortens the coagulation time so that the coagulation time approaches close to the value obtainable when 100% normal plasma is measured. Therefore, the graph shows a downward convex curve below a straight line (dotted line) that connects the points corresponding to 100% test plasma and 100% normal plasma (FIG. 1(A)).

When a coagulation factor inhibitor is present in a test plasma, the relevant coagulation factor inhibitor inactivates coagulation factors in the added normal plasma, even though the proportion of addition of normal plasma is increased. Therefore, the extent of improvement in the coagulation time due to the addition of normal plasma is low, and a curve that is convex upward is shown (FIG. 1(B)).

As a coagulation factor inhibitor which affects the sensitivity of the reagent for blood coagulation time measurement, lupus anticoagulant (hereinafter, LA) is known. LA is defined as an immunoglobulin which inhibits a phospholipid-dependent coagulation reaction in vitro without inhibiting the activity of individual coagulation factors, and is not a single antibody. Since the presence of phospholipids is essential to the coagulation reaction, usually, many of the reagents for blood coagulation time measurement are rich in phospholipids. LA reacts with phospholipids in the reagents, thereby consuming these phospholipids, and consequently inhibits the coagulation reaction to prolong the coagulation time. Therefore, the results of coagulation tests such as PT and APTT are often found to be abnormal. However, since LA varies in reaction intensities depending on the type of phospholipids (origin, phospholipid composition, and the like), it is known that different results of determination on LA positivity/negativity are obtained depending on the reagent for blood coagulation time measurement to be used.

DOCUMENT OF RELATED ART

Non-Patent Document

Non-Patent Document 1: Kensa to Gijutsu (Examination and Technology), Vol. 34, no. 8, August 2006, p. 735-742
Non-Patent Document 2: Update of the guidelines for lupus anticoagulant detection, Journal of Thrombosis and Haemostasis, 7: pp. 1737-1740, 2009

DISCLOSURE OF INVENTION

Problem to be Solved by the Invention

Regarding the anticoagulant therapy, heparin that has prompt efficacy and can be intravenously administered is used at the time of emergency, and warfarin that is a peroral anticoagulant is used for the prevention based on long-term administration. Between these, warfarin is known to suppress biosynthesis in the liver of Factor II (prothrombin), Factor VII, Factor IX and Factor X among blood coagulation factors by antagonizing the action of vitamin K in vivo. Therefore, in the cases of warfarin takers, people who suffer from vitamin K deficiency, or hepatic failure patients (patients who suffer from hepatic cirrhosis, fulminant hepatitis or chronic hepatitis, and the like), when conventional methods for identifying the cause of prolongation of the blood coagulation time by the mixing test is used, it is not clearly identified whether the prolongation is a prolongation of the coagulation time based on antiphospholipid antibody such as LA, or a prolongation of the coagulation time based on the action of warfarin, deficiency of vitamin K, or deficiency of the blood coagulation factors based on hepatic failure, and discrimination of the cause has been difficult. This problem becomes more serious in the case of patients who receive warfarin administration and are LA-positive. It is because when LA positivity is determined or suspected, and anticoagulation therapy is initiated, LA detection, and monitoring and tracing of the increase and decrease of LA are important, but these cannot be conducted accurately.

It is recommended by the International Society on Thrombosis and Haemostasis (ISTH) that at the time of LA detection, measurement be made after the test plasma is mixed with an equal amount of a healthy person's plasma in order to supplement any insufficient coagulation factors. Here, regarding the healthy person's plasma thus used, plasmas that have been subjected to double centrifugation so that the number of blood platelets is less than $10^7$/mL, and have been conditioned such that the activity of all of the blood coagulation factors is almost 100%, are prepared in-house in various facilities and used (Non-Patent Document 2). However, among the blood coagulation factors, there are factors which have very unstable activity and are prone to be inactivated. Thus, it is very difficult to prepare such a healthy person's plasma while maintaining the activity of all the blood coagulation factors to be almost 100%, and there is a problem that stable acquisition thereof is not easy. Furthermore, in the preparation of a healthy person's plasma, as the number of people whose plasmas are stored (pooled) and mixed increases, the variations in individuals of the activity of the coagulation factors can be averaged. However, the required number of healthy people cannot be secured in some facilities, and since deviations occur in the plasma suppliers, there is a problem that differences in the product quality may occur among different batches. Furthermore, in the method of using a healthy person's plasma, not only the LA in the test plasma is diluted, but also substances that inhibit the measurement of LA contained in the healthy person's plasma (phospholipids, platelet-derived disrupted membranes, and the like) may be incorporated. Particularly in the case where LA is weakly positive, there is a problem that there is a possibility of false negativity being detected.

Therefore, there has been a strong demand for the development of a method of measuring the blood coagulation time, in which even for warfarin takers, people who suffer from vitamin K deficiency, or hepatic failure patients, LA detection can be carried out easily with high sensitivity as compared with the method recommended by the ISTH as described above, without being affected by deficiency of the blood coagulation factors.

Means for Solving Problem

The inventors of the present invention conducted a thorough investigation, and as a result, the inventors found that when the blood coagulation time is measured after a specific blood coagulation factor is added to a sample to be tested (for example, plasma), the blood coagulation time for detection can be measured conveniently and sensitively, even if a healthy person's plasma is not used. Thus, the inventors completed the present invention.

That is, the present invention provides a method of measuring the blood coagulation time for LA detection, the method including adding a buffer solution composition containing blood coagulation factors to a blood sample before measurement or at the time of measurement of the blood coagulation time, and measuring the blood coagulation time.

Furthermore, the present invention provides an auxiliary reagent including, as a main ingredient, a buffer solution composition containing blood coagulation factors, which auxiliary reagent is used in combination with a reagent for blood coagulation time measurement to detect lupus anticoagulant.

Furthermore, the present invention provides a reagent kit for blood coagulation time measurement to detect lupus anticoagulant, the reagent kit containing the following (A) and (B):
(A) a reagent for activated partial thromboplastin time measurement or a reagent for diluted Russell's viper venom time measurement; and
(B) an auxiliary reagent containing, as a main ingredient, a buffer solution composition containing blood coagulation factors.

Effect of the Invention

According to the method of the present invention, even in the case where vitamin K-dependent coagulation factors (FII, FVII, FIX and FX) are deficient, for example, in blood samples derived from warfarin takers, people who suffer from vitamin K deficiency, or hepatic failure patients (patients who suffer from hepatic cirrhosis, acute hepatitis or chronic hepatitis, and the like), the presence or absence of LA can be checked conveniently and sensitively. Therefore, right therapeutic policies for patients with LA can be determined. Furthermore, since it is not necessary to prepare a healthy person's plasma, the problem that there are differences among different batches of healthy persons' plasmas, which has been hitherto problematic, and the problem that stable acquisition is difficult, can also be solved. Furthermore, what should be specially mentioned for the method of the present invention is that LA, for which there has been hitherto a possibility of being overlooked even by a mixing test with a healthy person's plasma, can be detected conveniently and sensitively. This is a completely surprising effect which cannot be predicted in the simple idea of carrying out the conventional addition of normal plasma by replacement and addition of individual plasma components.

BRIEF DESCRIPTION OF DRAWINGS

FIG. 1(A) presents the pattern of coagulation factor deficiency; FIG. 1(B) presents the pattern of coagulation factor inhibitor type; and FIG. 1(C) presents the pattern of a case in which the cause of prolongation of the coagulation time is unknown.

BEST MODE FOR CARRYING OUT THE INVENTION

Figure 1:
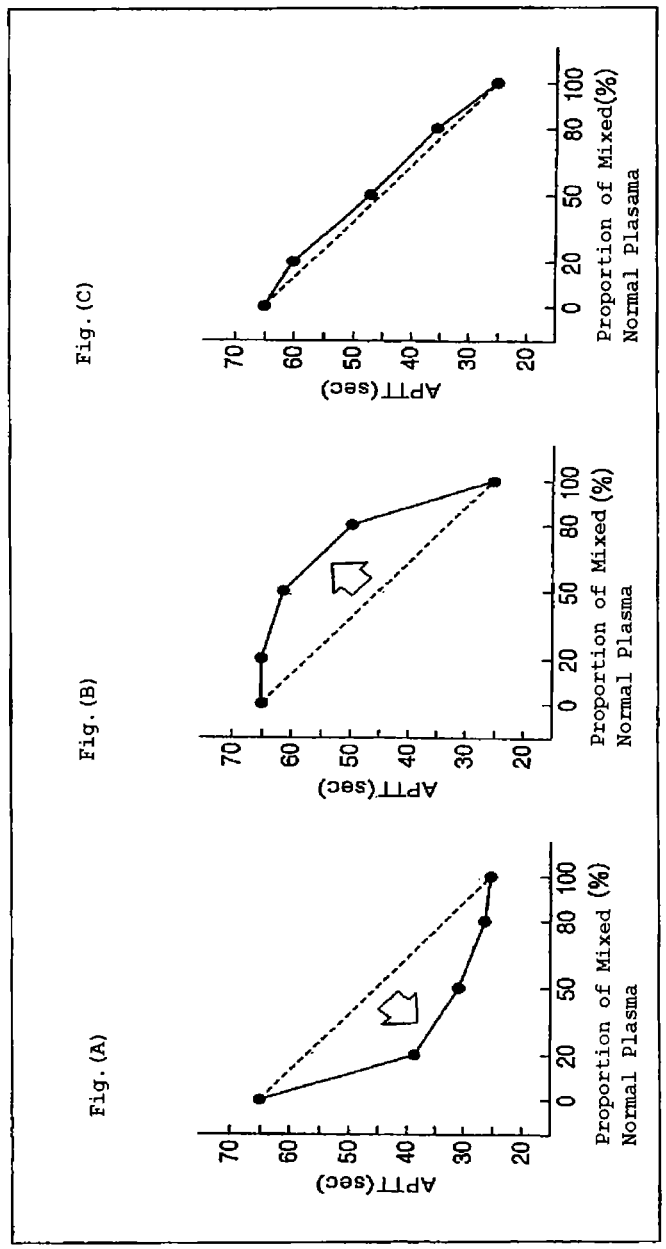
FIG. 1 is a model diagram illustrating the results of a mixing test according to a conventional method.

The method of measuring the blood coagulation time for LA detection of the present invention is characterized in that a buffer solution composition containing blood coagulation factors is added to a blood sample before measurement or at the time of measurement of the blood coagulation time.

The blood sample that is used in the method of the present invention is preferably whole blood or plasma, and usually, the blood sample is prepared by adding an anticoagulant such as sodium citrate to the blood collected from a subject. Among such blood samples, in the case of dealing with blood samples derived from those subjects for whom conventional LA detection has been difficult, the method of the present invention is particularly useful. Examples of such a blood sample include blood samples derived from warfarin takers, people who suffer from vitamin K deficiency, and hepatic failure patients.

Regarding the means of measuring the blood coagulation time, that is, the reagent for blood coagulation time measurement, any phospholipid-dependent reagent or measuring means both for blood coagulation time measurement and exhibiting sensitivity to LA may be used, and any known reagent of measuring the prothrombin time (PT), activated partial thromboplastin time (APTT), diluted PT (dPT), diluted APTT (dAPTT), kaolin clotting time (KCT), diluted Russell's viper venom time (dRVVT) and the like can be used. Among these reagents, for example, the main components of the reagent for measuring the prothrombin time (PT) are calcium and tissue thromboplastin; the main components of the reagent of measuring the activated partial thromboplastin time (APTT) are phospholipids, contact factor-activating agents (negatively charged bodies such as kaolin, anhydrous silicic acid, and ellagic acid) and calcium; the main components of the reagent of measuring the kaolin clotting time (KCT) are kaolin and calcium; and the main components of the reagent of measuring the diluted Russell's viper venom time (dRVVT) are Russell's viper venom and phospholipids. These components can be used as appropriately independent reagents, or as mixed reagents. Also, for the reagents described above, commercially available products can be used in all cases. Examples of the reagents for PT measurement that are commercially available include COAGPIA (registered trademark) PT-S (manufactured by SEKISUI MEDICAL CO., LTD.), THROMBOCHECK PT PLUS (manufactured by Sysmex Corp.), and STA Reagent Series PT (manufactured by Roche Diagnostics GmbH). Examples of the reagents for APTT measurement that are commercially available include COAGPIA (registered trademark) APTT-N (manufactured by SEKISUI MEDICAL CO., LTD.), THROMBOCHECK APTT-SLA (manufactured by Sysmex Corp.), APTT Liquid RD and PTT LA reagent "RD" (manufactured by Roche Diagnostics GmbH). Examples of the form of the reagent include a dried form that is dissolved at the time of use, and a solution form.

One or more of these reagents and the buffer solution composition containing blood coagulation factors (auxiliary reagent) of the present invention can also be combined into a kit.

Among these reagents for blood coagulation time measurement, PT, APTT or dRVVT is preferred from the viewpoint of the sensitivity of LA detection. Furthermore, in the case of measuring the PT or APTT, it is preferable to employ a mixing test using normal plasma and a test plasma. In the case of measuring the dRVVT, a mixing test does not have to be particularly carried out.

Regarding the buffer solution composition containing blood coagulation factors that is used in the present invention, a buffer solution composition containing at least one of the blood coagulation factors that are considered to be deficient in the blood sample to be tested may be used. The buffer solution composition is preferably a buffer solution composition containing one kind or two or more kinds selected from FII, FVII, FVIII, FIX, FX, FXI and FXII, and more preferably a buffer solution composition containing at least one kind or two or more kinds selected from FII, FVII, FIX, and FX. Furthermore, in the case of measuring the PT, a buffer solution containing one kind or two or more kinds selected from FII, FVII and FX is preferred. In the case of measuring the APTT, a buffer solution composition containing one kind or two or more kinds selected from FII, FVIII, FIX, FX, FXI, and FXII is preferred, and particularly, a buffer solution composition containing one kind or two or more kinds selected from FIX and FX is preferred. Furthermore, in the case of measuring the dRVVT, a buffer solution composition containing one kind or two or more kinds selected from FII and FX is preferred. In the case where when the buffer solution composition of the present invention is added to a sample to be tested, the sample is diluted by the buffer solution composition, and the blood coagulation factor concentration in the sample is decreased to thereby affect the coagulation time, blood coagulation factors that need to be supplemented in accordance with the reagent used may be incorporated into the buffer solution composition described above. For example, FVIII, FXI, and FXII may be incorporated for the APTT, dAPTT, and KCT; FVII may be incorporated for the PT; and FX may be incorporated for the dRVVT.

Here, as the buffer solution, a known buffer solution such as a good buffer solution such as HEPES can be appropriately used. The pH of the buffer solution may be any pH that does not deactivate the blood coagulation factors contained in the buffer solution composition, and the pH is preferably pH 6 to 9, and more preferably pH 6.5 to 8.0. Furthermore, the concentration of the buffer solution may be any concentration as long as the buffering capacity during storage is maintained, and the concentration is preferably 5 mM to 100 mM, and more preferably 5 mM to 50 mM.

The concentration of blood coagulation factors in the buffer solution composition is, as the concentration of blood coagulation factors after the buffer solution composition has been added to a blood sample, preferably in the range of 0.01 U/mL to 10 U/mL, and more preferably in the range of 0.1 U/mL to 5 U/mL. The mixing ratio of the blood sample and the buffer solution composition may be appropriately set in consideration of the concentration of blood coagulation factors in the buffer solution composition. The dilution ratio of the blood sample by the buffer solution composition is preferably 3 times or less, and more preferably 2 times or less.

Furthermore, in the buffer solution composition, a compound known as a stabilizer for the blood coagulation factors may also be appropriately added. For example, glycylglycine, glycylglycylglycine, and the like that are disclosed in Japanese Patent Application Publication (JP-B) No. 06-050999 may be added. Furthermore, a preservative, an ion intensity adjusting agent, and the like may also be added as long as the effects of the present invention are not impaired.

In the method of the present invention, a buffer solution composition containing the blood coagulation factors is added to a blood sample before measurement or at the time of measurement of the blood coagulation time. Here, adding the buffer solution composition before the measurement of the blood coagulation time corresponds to a pretreatment of the blood sample. That is, the buffer solution composition is added to a blood sample to pretreat the blood sample, and then the blood coagulation time is measured using a reagent for blood coagulation measurement. On the other hand, adding the buffer solution composition at the time of measurement of the blood coagulation time corresponds to a process of adding the buffer solution composition to a portion of the reagent for blood coagulation measurement and measuring the blood coagulation time. Between these timings of addition, it is preferable to add the buffer solution composition to the blood sample before the measurement of the blood coagulation time, from the viewpoint that storage stability of the coagulation factors incorporated in the buffer solution composition is easily secured.

Regarding the method of measuring the blood coagulation time, for example, a method of detecting coagulation by measuring an optical change such as a change in transmitted light or a change in scattered light, which changes along with a blood coagulation reaction that occurs as a result of adding a reagent containing calcium and phospholipids (reagent for blood coagulation time measurement) to a blood sample, or by physically measuring the viscosity of the measurement sample, can be suitably used.

Regarding calcium, it is preferable to use a salt between an inorganic acid and calcium. Examples of such a calcium salt include calcium chloride. Furthermore, examples of a calcium salt other than a salt between an inorganic acid and calcium include calcium lactate. The concentration of calcium in the reagent for blood coagulation time measurement can be appropriately set according to the kind of the method of measuring the blood coagulation time. For example, in the case of the APTT measurement method, the concentration of calcium is preferably about 20 mM to 25 mM, and in the case of the PT measurement method, the concentration of calcium is preferably 10 mM to 12.5 mM.

Regarding phospholipids, phospholipids that have been hitherto used in reagents for blood coagulation time measurement can be suitably used. There are no particular limitations on the fatty acid side chains of the phospholipids, but palmitic acid, oleic acid, and stearic acid are preferred. Examples of the phospholipids include phosphatidylserine, phosphatidylethanolamine, and phosphatidylchloline. Furthermore, the phospholipids may be naturally occurring phospholipids such as bovine brain-derived, rabbit brain-derived, human placenta-derived, and soybean-derived phospholipids, or may be phospholipids produced by genetic engineering. The concentration of phospholipids in a measurement sample is preferably, for example, 1 μg/mL to 200 μg/mL in an APTT reagent, 10 μg/mL to 300 μg/mL in a PT reagent, and 1 μg/mL to 300 μg/mL in a dRVVT measuring reagent.

The pH of the reagent for blood coagulation time measurement can be appropriately set in consideration of the pH at the time when the reagent is mixed with the buffer solution composition of the present invention; however, the pH of the reagent for measurement itself is preferably pH 6.0 to 8.0, and more preferably pH 7.0 to 7.6. The pH can be appropriately regulated using a buffer agent that is used in conventional reagents for blood coagulation time measurement. Examples of the buffer agent include HEPES and TRIS, but the examples are not limited to these.

The reagent for blood coagulation time measurement may contain a component that is contained in conventionally known reagents for blood coagulation time measurement, in addition to the components described above. Examples of such a component include an activating agent, snake venom, and tissue factors. Examples of the activating agent include ellagic acid, kaolin, Celite, colloidal silica, anhydrous silicic acid, alumina, and magnesium. Examples of the snake venom include Russell's viper venom, Textarin snake venom, and Ecarin snake venom. Examples of the tissue factors include natural tissue thromboplastins such as rabbit brain-derived, human placenta-derived, and bovine brain-derived tissue thromboplastins; and genetically recombined tissue thromboplastin.

The method of the present invention can also be applied to the blood coagulation correction test (mixing test) described in Non-Patent Document 1. That is, the method can be applied to a method of adding a normal blood sample to a blood sample to be tested, and determining the extent to which the blood coagulation time is corrected, by plotting a graph.

More particularly, for example, a plasma sample diluted by adding Pooled Normal Plasma (manufactured by Precision Biologic, Inc.; hereinafter, abbreviated to PNP) as normal plasma or the buffer solution composition of the present invention to the test plasma at 1:1, is used as a sample to be tested. Samples were prepared by adding normal plasma to this sample to be tested, and mixing this sample to be tested with the normal plasma such that the proportions of the normal plasma are 0%, 20%, 50%, 80%, and 100%, and measurement of the APTT is carried out. The results are plotted into a graph (horizontal axis: proportion of normal plasma mixed, or proportion of the test plasma (%); vertical axis: coagulation time (seconds)), and the blood coagulation time can be visually determined from the shape of the graph.

When the method of the present invention is used, it is simply required to carry out the conventional measurement of the blood coagulation time, except that merely the buffer solution composition described above is added, and thereby the presence or absence of LA can be accurately detected and determined even with a blood sample derived from a warfarin taker, a person who suffers from vitamin K deficiency, or a hepatic failure patient.

The buffer solution composition containing blood coagulation factors can be used as an auxiliary reagent that is used in combination with a reagent for blood coagulation time measurement to detect lupus anticoagulant.

Furthermore, a combination of (A) a reagent for activated partial thromboplastin time measurement or a reagent for diluted Russell's viper venom time measurement, with (B) an auxiliary reagent including a buffer solution composition containing blood coagulation factors as a main ingredient, is useful as a reagent kit for blood coagulation time measurement to detect lupus anticoagulant.

EXAMPLES

The present invention will be described in more detail by way of the following Examples, but the present invention is not intended to be limited to the following Examples.

Example 1

A test plasma was diluted with each of the auxiliary reagents described in Table 1 at 1:1, and the mixtures were used as samples to carry out a conventional mixing test. A comparison was made between the shapes of curve in the graphs.

<Measurement Item>
(1) APTT Screening Test

Measurement was carried out using a PTT LA reagent, "RD" (manufactured by Roche Diagnostics GmbH), and an automatic blood coagulation analyzer, STA-R (manufactured by Roche Diagnostics GmbH). For determination, the cut-off value described in the package insert of the reagent was used. The relevant reagent is a reagent for carrying out the measurement using a self-made calcium chloride solution, apart from a PTT LA reagent containing cephalin which is a phospholipid, and silica which is a contact factor activating agent (negatively charged body). The reagent can be used for the method of the present invention in combination with the buffer solution composition containing blood coagulation factors (auxiliary reagent) of the present invention.

(2) dRVVT Test

Measurement was carried out using LA Test "GRADIPORE" (manufactured by Medical & Biological Laboratories Co., Ltd.) and an automatic blood coagulation analyzer, STA-R. For determination, the cut-off value described in the package insert of the reagent was used. The relevant reagent is composed of Reagent 1 containing Russell's viper venom and phospholipids, and Reagent 2 containing Russell's viper venom and an excess amount of phospholipids, and the reagent can be used for the method of the present invention in combination with the buffer solution composition containing blood coagulation factors (auxiliary reagent) of the present invention.

(3) Phospholipid Neutralization Test

Measurement was carried out using STACLOT LA (manufactured by Roche Diagnostics GmbH) reagent and a blood coagulation analyzer, ST4 (manufactured by Roche Diagnostics GmbH). For determination, the cut-off value described in the package insert of the reagent was used.

(4) Mixing Test

Measurement was carried out using a PTT LA reagent, "RD" (manufactured by Roche Diagnostics GmbH), and an automatic blood coagulation analyzer, CP2000 (manufactured by SEKISUI MEDICAL CO., LTD.). As normal plasma, Pooled Normal Plasma (hereinafter, PNP; Precision Biologic, Inc.) was used. The sample mixing proportion was set to 0%, 10%, 20%, 50% and 100%, and measurement was carried out by automatically diluting the sample using the mixing test function of CP2000. Determination was made such that a graph was drawn, and if the graph was convex upward, the sample was determined to be LA-positive. If determination was difficult, it was considered as pending determination.

(5) Modification of Mixing Test

Measurement was carried out in the same manner as in (4), by inserting samples obtained by diluting a test plasma with PNP or auxiliary reagents 1 to 4 that will be described below at a ratio of 1:1, into sample cups, and mounting the sample cups in CP2000. Determination was made such that a graph was drawn, and if the graph was convex upward, the sample was determined to be LA-positive. If determination was difficult, it was considered as pending determination.

<Buffer Solution Composition of Present Invention: Auxiliary Reagent>

Various auxiliary reagents were prepared by adding the blood coagulation factors indicated in Table 1 to HBS (50 mM HEPES pH 7.5, and 150 mM sodium chloride) as a base. For the blood coagulation factors, products manufactured by Haematologic Technologies, Inc. were used in all cases.

TABLE 1

Auxiliary reagent composition

| | Human Factor IX | Human Factor X | Human Factor XII | Human Factor VIII |
|---|---|---|---|---|
| Auxiliary reagent 1 | 2 U/mL | 2 U/mL | — | — |
| Auxiliary reagent 2 | 2 U/mL | 2 U/mL | — | 1 U/mL |
| Auxiliary reagent 3 | 2 U/mL | 2 U/mL | 2 U/mL | — |
| Auxiliary reagent 4 | 2 U/mL | 2 U/mL | 2 U/mL | 1 U/mL |

Auxiliary Reagent Composition

<Test Plasma>

Test plasmas A and B are both plasmas collected from patients who receive warfarin administration.

<Results>

As shown in Table 2, plasma A was positive in all of the LA examinations including the APTT screening test, the dRVVT test, and the phospholipid neutralization method. Plasma B was positive for LA in the APTT screening test and the dRVVT test.

TABLE 2

Results and determination of LA test

| Item | APTT screening | | dRVVT | | | | Phospholipid neutralization method | | | |
|---|---|---|---|---|---|---|---|---|---|---|
| Unit | sec | Determination | sec | sec | Ratio | Determination | sec | sec | Δsec | Determination |
| Cut-off value | 47 | | | | 1.3 | | | | 8 | |
| Plasma A | 143.0 | Positive | 220.4 | 82.5 | 2.67 | Positive | 132.0 | 86.0 | 46.0 | Positive |
| Plasma B | 57.4 | Positive | 77.9 | 54.8 | 1.42 | Positive | 47.7 | 47.8 | −0.1 | Negative |

Figure 2:
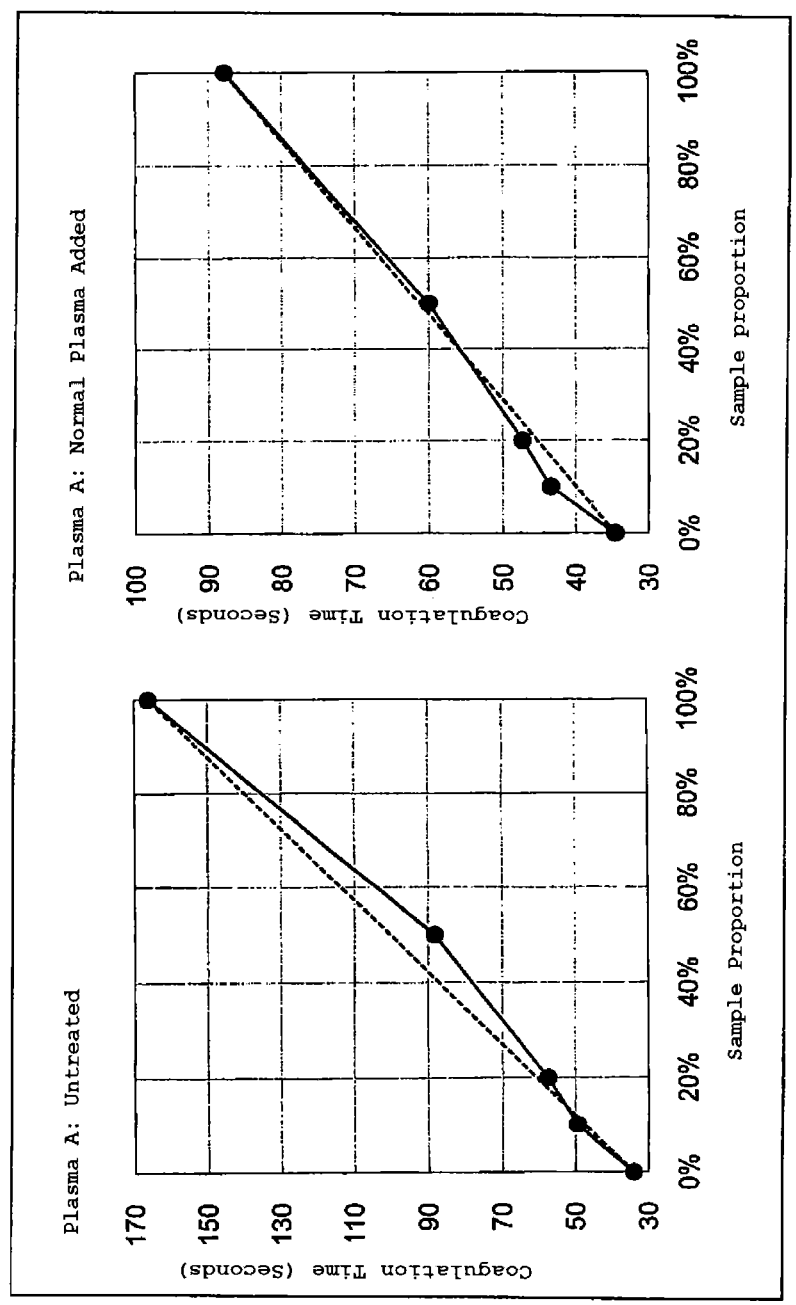
FIG. 2 is a diagram illustrating the results of a mixing test in the case of using untreated plasma A and normal plasma-added plasma A respectively as samples.
Figure 3:
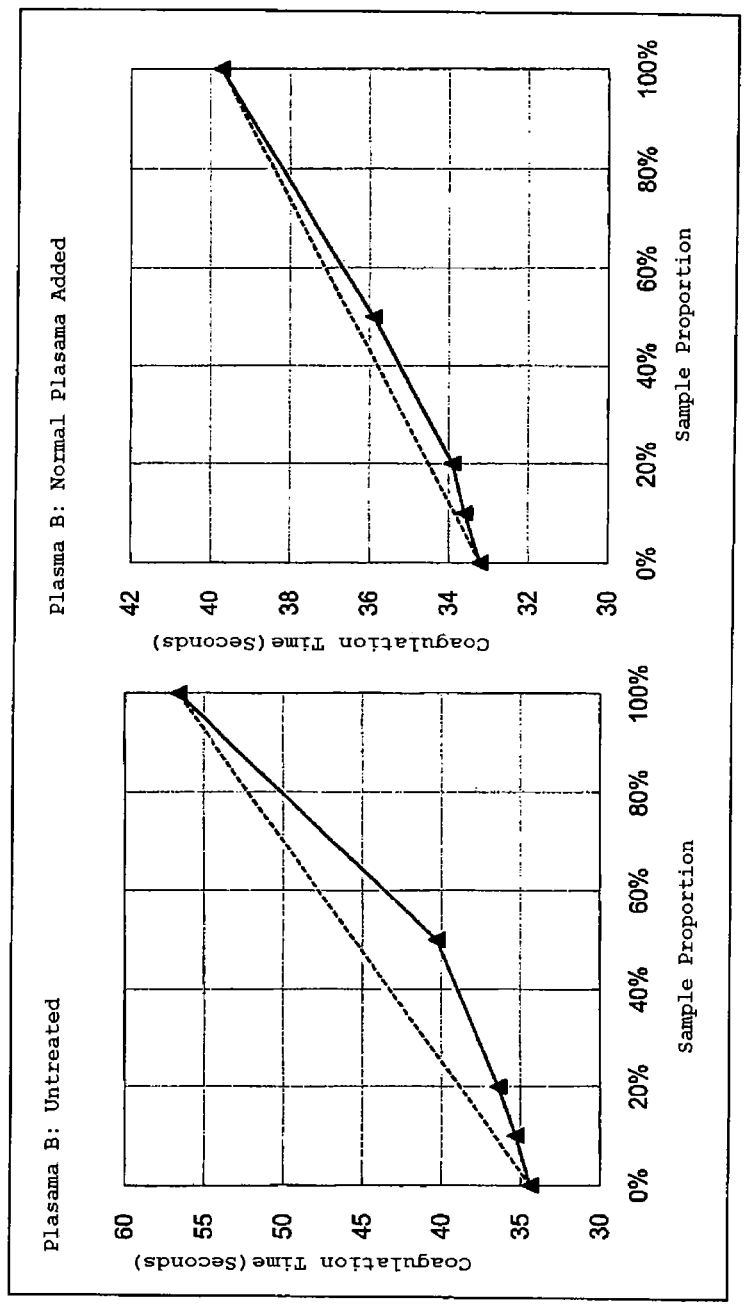
FIG. 3 is a diagram illustrating the results of a mixing test in the case of using untreated plasma B and normal plasma-added plasma B respectively as samples.
Figure 4:
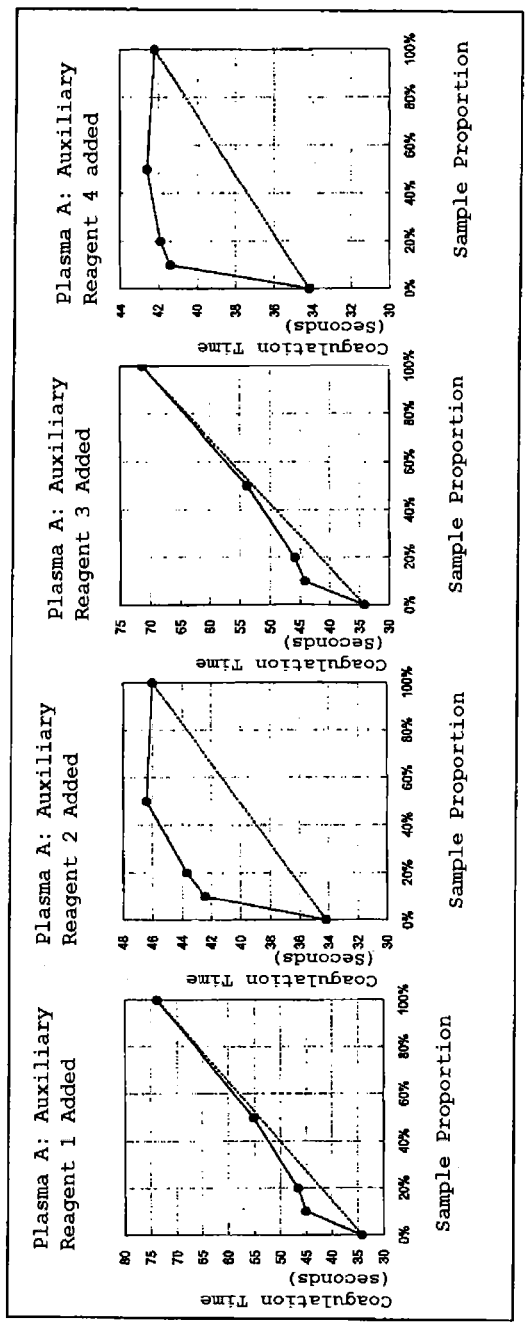
FIG. 4 is a diagram illustrating the results of a mixing test in the case of using plasma A to which auxiliary reagents 1 to 4 were added, as samples.
Figure 5:
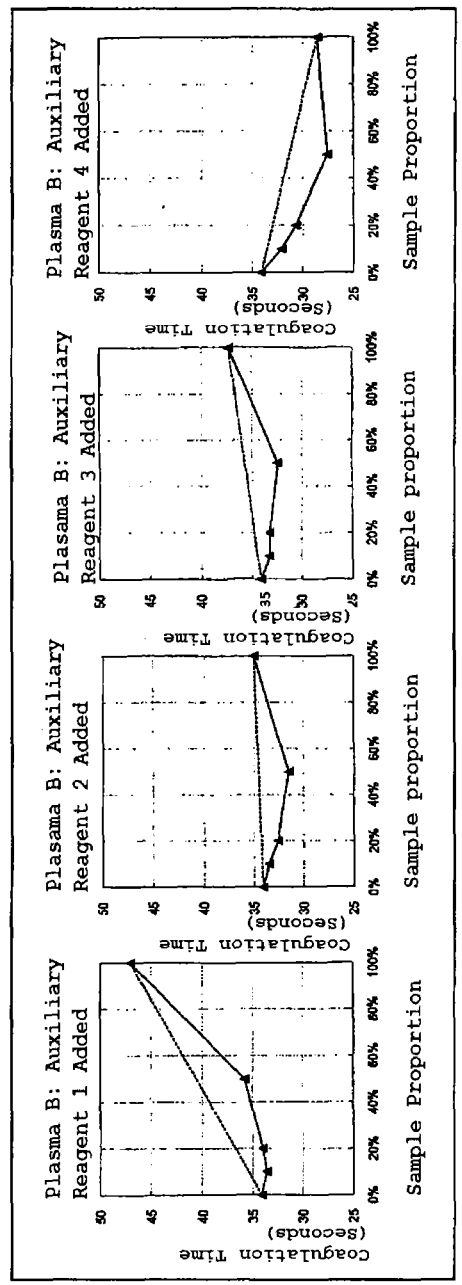
FIG. 5 is a diagram illustrating the results of a mixing test in the case of using plasma B to which auxiliary reagents 1 to 4 were added, as samples.

As indicated in the rows for Untreated in Table 3, the left diagram in FIG. 2, and the left diagram in FIG. 3, plasmas A and B both showed a tendency of being convex downward in the mixing test, and were determined to be LA-negative. Among the modifications of the mixing test, in the method of using normal plasma (PNP) that is generally recommended, plasma A gave an S-shaped graph which was almost close to a straight line, and it was difficult to determine whether the curve was convex upward or convex downward (in the row of Normal plasma added in Table 3, and the right diagram in FIG. 2). On the contrary, when the auxiliary reagents 1 to 4 of the present invention were used, plasma A gave graphs that were clearly convex upward, and thus it was easily determined to be positive (in the rows for Auxiliary reagents in Table 3, and FIG. 4). Plasma B gave graphs that were clearly convex downward, and it was determined to be negative (in the column of Auxiliary reagent in Table 3, and FIG. 5).

by the conventional mixing test or a modification of the mixing test. Furthermore, plasma B was positive in the APTT screening test and the dRVVT test, but it was determined that the determination was false positive in all cases due to warfarin administration, and was actually LA-negative.

Example 2

0.5 volume of the auxiliary reagent described below was added to 9.5 volume of a test plasma, and the components were mixed to prepare a measurement sample. Thus the sample was subjected to the dRVVT test, and thus the ratio of coagulation time was determined.
<Measurement Item>
(1) dRVVT Test
A dRVVT test was carried out using DVVtest (registered trademark) and DVVconfirm (all manufactured by Sekisui

TABLE 3

Mixing test and modification of mixing test

| Test plasma | Treatment | Determination | Sample proportion 0% | 10% | 20% | 50% | 100% |
|---|---|---|---|---|---|---|---|
| Plasma A | Untreated | Negative | 34.1 | 49.4 | 57.4 | 88.2 | 166.1 |
| | Normal plasma added | Pending determination | 34.6 | 43.4 | 47.3 | 60.0 | 87.8 |
| | Auxiliary reagent 1 added | Positive | 34.2 | 45.1 | 46.6 | 55.2 | 73.8 |
| | Auxiliary reagent 2 added | Positive | 34.2 | 42.4 | 43.7 | 46.4 | 46.0 |
| | Auxiliary reagent 3 added | Positive | 34.2 | 44.2 | 45.9 | 53.8 | 71.3 |
| | Auxiliary reagent 4 added | Positive | 34.2 | 41.4 | 41.9 | 42.6 | 42.2 |
| Plasma B | Untreated | Negative | 34.4 | 35.3 | 36.4 | 40.3 | 56.6 |
| | Normal plasma added | Negative | 33.2 | 33.6 | 33.9 | 35.9 | 39.7 |
| | Auxiliary reagent 1 added | Negative | 34.1 | 33.6 | 34.0 | 35.8 | 47.0 |
| | Auxiliary reagent 2 added | Negative | 34.1 | 33.5 | 32.6 | 31.5 | 35.0 |
| | Auxiliary reagent 3 added | Negative | 34.1 | 33.2 | 33.2 | 32.4 | 37.3 |
| | Auxiliary reagent 4 added | Negative | 34.1 | 32.1 | 30.7 | 27.6 | 28.6 |

According to the present invention, it was easily determined that the determination of negativity in the mixing test of plasma A was false negative due to warfarin administration, and was actually LA-positive. This could not be found Diagnostics, LLC) as reagents for blood coagulation time measurement, and using an incubation time for the measurement sample of 216 seconds and the APTT coagulation point parameters in an automatic blood coagulation analyzer, CP2000 (manufactured by SEKISUI MEDICAL CO., LTD.). The cut-off value (t/c) in the present Example was set to 1.3 or less, and detection and determination of LA was carried out. The relevant reagents were composed of DVVtest (registered trademark) reagent containing Russell's viper venom, phospholipids and calcium, and DVVconfirm reagent containing Russell's viper venom, an excess amount of phospholipids, and calcium. The reagents can be used in the method of the present invention in combination with the buffer solution composition containing blood coagulation factors (auxiliary reagent) of the present invention.

<Buffer Solution Composition of Present Invention: Auxiliary Reagent>

FX and FII were combined such that the concentration of FX would be 20 times the concentration described in the row of Table 4, and the concentration of FII would be 20 times the concentration described in the column of Table 4, and the factors were dissolved in HBS to prepare 28 different auxiliary reagents. For FX and FII, products of Haematologic Technologies, Inc. were used.

<Test Plasma>

As a LA-negative plasma without warfarin administration: L(−)W(−) plasma, AK CALIBRANT A (manufactured by Sysmex Corp.) was used; as a LA-negative plasma with warfarin administration: L(−)W(+) plasma, AK CALIBRANT D (manufactured by Sysmex Corp.) was used; as a LA-positive plasma without warfarin administration: L(+)W(−) plasma, Lupus Anticoagulant Plasma (manufactured by Trina Bioreactives AG) was used; and as a LA-positive plasma with warfarin administration: L(+)W(−) plasma, Lupus anticoagulant plasma (manufactured by Busicom, Inc.) was used.

<Results>

The results are presented in Table 4.

When none of FII and FX are not added (0 U/mL), it is determined such that:

the plasma of L(−)W(−) is LA-negative;

the plasma of L(−)W(+) is LA-negative;

the plasma of L(+)W(−) is LA-positive; and the plasma of L(+)W(+) is LA-negative, and results of LA false negativity were obtained for the plasma of L(+)W(+).

Furthermore, the plasma of L(−)W(+) was LA-negative, but the t/c value was 0.62, which was an abnormal value.

In this regard, when any one or more of FII and FX was added to various test plasmas, only the t/c value of the plasma of L(+)W(+) was increased to a value higher than or equal to the cut-off value, while maintaining the determination results for the plasma of L(−)W(−), the plasma of L(−)W(+), and the plasma of L(+)W(−). Thus, results of LA positivity that should be obtained were obtained.

Furthermore, when any one or more of FII and FX was added to the plasma of L(−)W(+), the t/c value approached close to 1, and it was confirmed that the influence of warfarin administration could be reduced. When this score and the score of the plasma of L(+)W(+) are taken into consideration, it is implied that the dRVVT test using the method of the present invention can accurately detect LA even in the case of warfarin being administered. Thus, the method of the present invention is very useful in, for example, the monitoring of the LA therapeutic effect during warfarin administration.

TABLE 4

| FX (U/mL) | LA | W | FII (U/mL) 0 t/c | 0.1 t/c | 0.2 t/c | 0.3 t/c | 0.4 t/c | 0.5 t/c |
|---|---|---|---|---|---|---|---|---|
| 0 | − | − | 1.04 | | | | | 1.14 |
|   | − | + | 0.62 | | | | | 0.86 |
|   | + | − | 2.21 | | | | | 2.16 |
|   | + | + | 1.26 | | | | | 2.22 |
| 0.1 | − | − | | 1.06 | 1.08 | 1.07 | 1.09 | 1.11 |
|   | − | + | | 0.84 | 0.90 | 0.91 | 0.94 | 0.97 |
|   | + | − | | 2.31 | 2.33 | 2.36 | 2.36 | 2.37 |
|   | + | + | | 1.95 | 2.21 | 2.35 | 2.40 | 2.43 |
| 0.2 | − | − | | 1.09 | 1.11 | 1.12 | 1.11 | 1.07 |
|   | − | + | | 0.88 | 0.92 | 0.90 | 0.93 | 0.94 |
|   | + | − | | 2.36 | 2.43 | 2.41 | 2.42 | 2.28 |
|   | + | + | | 2.10 | 2.39 | 2.37 | 2.54 | 2.09 |
| 0.3 | − | − | | 1.11 | 1.12 | 1.11 | 1.12 | 1.12 |
|   | − | + | | 0.89 | 0.98 | 0.93 | 0.97 | 0.99 |
|   | + | − | | 2.37 | 2.46 | 2.44 | 2.43 | 2.43 |
|   | + | + | | 2.05 | 2.39 | 2.40 | 2.47 | 2.51 |
| 0.4 | − | − | | 1.11 | 1.11 | 1.13 | 1.14 | 1.14 |
|   | − | + | | 0.87 | 0.94 | 0.96 | 0.99 | 1.03 |
|   | + | − | | 2.45 | 2.48 | 2.48 | 2.47 | 2.46 |
|   | + | + | | 2.13 | 2.30 | 2.49 | 2.59 | 2.58 |
| 0.5 | − | − | 1.11 | 1.10 | 1.12 | 1.12 | 1.14 | 1.14 |
|   | − | + | 0.98 | 0.97 | 0.88 | 0.95 | 1.00 | 1.02 |
|   | + | − | 2.35 | 2.35 | 2.37 | 2.46 | 2.47 | 2.45 |
|   | + | + | 2.06 | 1.99 | 2.20 | 2.43 | 2.57 | 2.65 |

According to the method of the present invention, even when the plasma of a (+) subject who was sometimes determined to be LA-negative (false negative) by dRVVT test, but is LA-positive (+) and also receives warfarin administration (+) (plasma of L(+)W(+)) was measured, the correct determination, i.e. LA-positive, was made without being affected by warfarin administration.

The invention claimed is:

1. A method of measuring a blood coagulation time to detect a lupus anticoagulant, the method comprising
   adding composition comprising at least one blood coagulation factor to a blood or plasma sample obtained from a subject, wherein the blood or plasma is diluted by the composition at a dilution ratio of 3 times or less, wherein the at least one blood coagulation factor is selected from the group consisting of FII, FV, FVII, FVIII, FIX, FX, FXI and FXII,
   wherein the composition is not a plasma or blood sample,
   wherein the composition comprises the blood coagulation factor in an amount of 0.01 U/ml to 10 U/ml and at least one of 4-(2-hydroxyethyl)-1-piperazineethanesulfonic acid (HEPES) and tris(hydroxymethyl)aminomethane (Tris); and
   wherein the composition is buffered at a pH of from 6 to 9; and
   measuring, with a reagent for measuring prothrombin time, activated partial thromboplastin time, or a diluted Russel's viper venom time by optical measurement or based on a change in viscosity, the blood coagulation time of (A) the blood or plasma sample to which the composition is added and (B) a dilution of the blood or plasma sample to which the composition is added to determine the blood coagulation time and the presence of the lupus anticoagulant.

2. The method of claim 1, wherein the blood or plasma sample is whole blood or plasma.

3. The method of claim 1, wherein the composition buffered at a pH of from 6 to 9 is added to the blood or plasma sample before the measurement of the blood coagulation time.

4. The method of claim 1, wherein measuring the blood coagulation time comprising measuring an activated partial thromboplastin time or a diluted Russell's viper venom time.

5. The method of claim 1, comprising adding the composition comprising a blood coagulation factor to the blood sample and the blood sample is whole blood.

6. The method of claim 1, comprising adding the composition comprising a blood coagulation factor to the plasma sample.

7. The method of claim 1, wherein the composition buffered at a pH of from 6 to 9 is added to the blood or plasma sample at the time of measurement of the blood coagulation time.

8. The detection method according to claim 1, wherein the at least one blood coagulation factors is FII.

9. The detection method according to claim 8, further comprising a second blood coagulation factor that is FX.

10. The detection method according to claim 9, further comprising a second blood coagulation factor that is FIX.

11. The detection method according to claim 1, wherein the at least one blood coagulation is FIX.

12. The detection method according to claim 1, wherein the at least one blood coagulation factor is FX.

13. The detection method according to claim 12, further comprising a second blood coagulation factor that is FX.

14. The detection method according to claim 4, wherein the measuring of the blood coagulation time comprises measuring activated thromboplastin time.

15. The detection method according to claim 4, wherein the measuring of the blood coagulation time comprises a diluted Russell's viper venom time.

16. The detection method according to claim 1, wherein the composition comprises the blood coagulation factor in an amount of 0.1 to 5 U/ml.

17. The detection method according to claim 1, wherein the composition comprises a HEPES buffer.

18. The detection method according to claim 1, wherein the subject has been given warfarin or heparin before measurement or at a time of measurement of the blood coagulation time.

* * * * *